US006697674B2

(12) United States Patent
Leysieffer

(10) Patent No.: US 6,697,674 B2
(45) Date of Patent: Feb. 24, 2004

(54) AT LEAST PARTIALLY IMPLANTABLE SYSTEM FOR REHABILITATION OF A HEARING DISORDER

(75) Inventor: Hans Leysieffer, Taufkirchen (DE)

(73) Assignee: Cochlear Limited, Lane Cover (AU)

( * ) Notice: Subject to any disclaimer, the term of this patent is extended or adjusted under 35 U.S.C. 154(b) by 204 days.

(21) Appl. No.: 09/833,642

(22) Filed: Apr. 13, 2001

(65) Prior Publication Data

US 2001/0031996 A1 Oct. 18, 2001

(30) Foreign Application Priority Data

Apr. 13, 2000 (DE) .......................................... 100 18 334

(51) Int. Cl.$^7$ ................................................. A61N 1/18
(52) U.S. Cl. ........................................... 607/57; 600/25
(58) Field of Search ............................. 607/55–57, 137, 607/3; 600/25; 181/129–135; 381/312

(56) References Cited

U.S. PATENT DOCUMENTS

| 3,557,775 A | 1/1971 | Mahoney |
| 3,712,962 A | 1/1973 | Epley |
| 3,764,748 A | 10/1973 | Branch et al. |
| 4,352,960 A | 10/1982 | Dormer et al. |
| 4,441,210 A | 4/1984 | Hochmair et al. |
| 4,988,333 A | 1/1991 | Engebretson et al. |

(List continued on next page.)

FOREIGN PATENT DOCUMENTS

| DE | 296 16 956 | 2/1997 |
| EP | 0 190 836 | 8/1986 |
| EP | 0 200 321 | 11/1986 |
| EP | 0 263 254 | 4/1988 |
| EP | 0 400 630 | 12/1990 |
| EP | 0 499 940 | 8/1992 |
| EP | 0 537 385 | 4/1993 |
| EP | 0 823 188 | 10/1996 |
| WO | WO 90/07251 | 6/1990 |

OTHER PUBLICATIONS

H. Knoer, "Tinnitus Retraining Therapy and Hearing Acoustics", pp. 26–27, Feb. 1997, Journal "Hörakustik".
E. Lehnhardt, "Intracochlear Placement of Cochlear Implant Electrodes in Soft Surgery Technique", pp. 356–359, 1993, HNO 41.
H. Leysieffer et al., "A Totally Implantable Hearing Device for the Treatment of Sensorineural Hearing Loss", pp. 853–863, 1998, TICA LZ 3001, in HNO vol. 46.
J. Müller–Deile et al., "Cochlear Implant Supply For Non–Deaf Patients?", pp. 136–143, 1998, Laryngo–Rhino–Otol. 77.
J. Suzuki et al., Implantation of Partially Implantable Middle Ear Implant and the Indication, pp. 160–166, Karger Basel, 1988, Advances in Audiology, vol. 4.
S. Ruh et al., "Cochlear Implant for Patients with Residual Hearing", pp. 347–350, 1997, Laryngo–Rhino–Otol. 76.

(List continued on next page.)

Primary Examiner—Jeffrey R. Jastrzab
(74) Attorney, Agent, or Firm—Nixon Peabody LLP; David S. Safran

(57) ABSTRACT

An at least partially implantable system for rehabilitation of a hearing disorder which has at least one sensor (microphone) for picking up an acoustic signal and converting it into corresponding electrical signals, an electronic signal processing unit for audio signal processing and amplification, an electrical power supply unit which supplies energy to individual components of the system, and an output-side actory stimulation arrangement. The output-side stimulation arrangement includes an electromechanical transducer for mechanical stimulation of the middle ear or inner ear and an intracochlear, electrically acting stimulation electrode array with at least one stimulation electrode for electrical stimulation of the inner ear.

42 Claims, 7 Drawing Sheets

U.S. PATENT DOCUMENTS

| | | |
|---|---|---|
| 5,015,224 A | 5/1991 | Maniglia |
| 5,015,225 A | 5/1991 | Hough et al. |
| 5,070,535 A | 12/1991 | Hochmair et al. |
| 5,095,904 A | 3/1992 | Seligman et al. |
| 5,271,397 A | 12/1993 | Seligman et al. |
| 5,277,694 A | 1/1994 | Leysieffer et al. |
| 5,279,292 A | 1/1994 | Baumann et al. |
| 5,360,388 A | 11/1994 | Spindel et al. |
| 5,411,467 A | 5/1995 | Hortmann et al. |
| 5,545,219 A | 8/1996 | Kuzma |
| 5,578,084 A | 11/1996 | Kuzma et al. |
| 5,597,380 A | 1/1997 | McDermott et al. |
| 5,601,617 A | 2/1997 | Loeb et al. |
| 5,603,726 A | 2/1997 | Schulman et al. |
| 5,624,376 A | 4/1997 | Ball et al. |
| 5,626,629 A | 5/1997 | Faltys et al. |
| 5,772,575 A | 6/1998 | Lesinski et al. |
| 5,795,287 A | 8/1998 | Ball et al. |
| 5,800,475 A | 9/1998 | Jules |
| 5,814,095 A | 9/1998 | Müller et al. |
| 5,941,814 A | 8/1999 | Lehner et al. |
| 5,951,601 A | 9/1999 | Lesinski et al. |
| 5,957,958 A | 9/1999 | Schulman et al. |
| 5,977,689 A | 11/1999 | Neukermans |
| 5,984,859 A | 11/1999 | Lesinski |
| 5,999,632 A | 12/1999 | Leysieffer et al. |
| 6,038,484 A | 3/2000 | Kuzma |
| 6,123,660 A | 9/2000 | Leysieffer |
| 6,131,581 A | 10/2000 | Leysieffer et al. |
| 6,162,169 A | 12/2000 | Leysieffer |
| 6,198,971 B1 * | 3/2001 | Leysieffer .................... 607/55 |
| 6,227,204 B1 | 5/2001 | Baumann et al. |
| 6,251,062 B1 | 6/2001 | Leysieffer |
| 6,259,951 B1 * | 7/2001 | Kuzma et al. ................ 607/57 |

OTHER PUBLICATIONS

N. Yanagihara et al., "Implantable Hearing Aid", pp. 869–872, Aug. 1987, Arch Otolaryngal Head Neck Surg—vol. 113.

H.P. Zenner et al., "First Implantations of a Totally Implantable Electronic Hearing System for Sensorineural Hearing Loss", pp. 844–852, 1998, HNO vol. 46.

H.P. Zenner et al., "Active Electronic Hearing Implants for Patients with Conductive and Sensorineural Hearing Loss—a New Era of Ear Surgery", pp. 749–757, 1997, HNO vol. 45.

H.P. Zenner et al., "Totally Implantable Hearing Device for Sensorineural Hearing Loss", p. 1751, Nov. 28, 1998, The Lancet, vol. 352, No. 9142.

* cited by examiner

AT LEAST PARTIALLY IMPLANTABLE SYSTEM FOR REHABILITATION OF A HEARING DISORDER

BACKGROUND OF THE INVENTION

1. Field of the Invention

This invention relates to an at least partially implantable system for rehabilitation of a hearing disorder which comprises at least one sensor (microphone) for picking up an acoustic signal and converting it into the corresponding electrical signals, an electronic signal processing unit for audio signal processing and amplification, an electrical power supply unit which supplies individual components of the system with current, and an output-side actoric stimulation arrangement.

2. Description of Related Art

The expression "hearing disorder" is defined here as inner ear damage, combined inner ear and middle ear damage, and a temporary or permanent noise impression (tinnitus).

In recent years rehabilitation of sensorineural hearing disorders with partially implantable electronic systems has acquired major importance. In particular this applies to the group of patients in which hearing has completely failed due to accident, illness or other effects or is congenitally nonfunctional. If in these cases only the inner ear (cochlea) and not the neural auditory path which leads to the brain is affected, the remaining auditory nerve can be stimulated with electrical stimulation signals and thus a hearing impression can be produced which can lead to speech comprehension. In these so-called cochlear implants (CI) an array of stimulation electrodes which is controlled by an electronic system (electronic module) is inserted into the cochlea. This electronic module is encapsulated hermetically tightly and biocompatibly and is surgically embedded in the bony area behind the ear (mastoid). The electronic system, however, contains essentially only decoder and driver circuits for the stimulation electrodes. Acoustic sound reception, conversion of this acoustic signal into electrical signals and their further processing always take place externally in a so-called speech processor which is worn outside on the body. The speech processor converts the preprocessed signals coded accordingly onto a high frequency carrier signal which via inductive coupling is transmitted through the closed skin (transcutaneously) to the implant. The sound-receiving microphone always is located outside of the body and in most applications in a housing of a behind-the-ear hearing aid worn on the external ear and is connected to the speech processor by a cable. Such cochlear implant systems, their components and the principles of transcutaneous signal transmission are described, by way of example, in published European Patent Application EP 0 200 321 A2 and in U.S. Pat. Nos. 5,070,535, 4,441,210, 5,626,629, 5,545,219, 5,578,084, 5,800,475, 5,957,958 and 6,038,484. Processes of speech processing and coding in cochlear implants are described, for example, in published European Patent Application EP 0 823 188 A1, in European Patent 0 190 836 B1 and in U.S. Pat. Nos. 5,597,380, 5,271,397, 5,095,904, 5,601,617 and 5,603,726.

In addition to rehabilitation of congenitally deaf persons and those who have lost their hearing using cochlear implants, for some time there have been approaches to offer better rehabilitation than with conventional hearing aids to patients with a sensorineural hearing disorder which cannot be surgically corrected by using partially or totally implantable hearing aids. The principle consists in most embodiments in stimulating an ossicle of the middle ear or directly the inner ear via mechanical or hydromechanical stimulation and not via the amplified acoustic signal of a conventional hearing aid in which the amplified acoustic signal is supplied to the external auditory canal. The actuator stimulus of these electromechanical systems is accomplished with different physical transducer principles such as for example by electromagnetic and piezoelectric systems. The advantage of these devices is seen mainly in the sound quality which is improved compared to conventional hearing aids and for totally implanted systems in the fact that the hearing prosthesis is not visible. These partially and fully implantable electromechanical hearing aids are described, for example, by Yanigahara et al. "Implantable Hearing Aid", Arch Otolaryngol Head Neck Surg-Vol 113, 1987, pp. 869–872; Suzuki et al. "Implantation of Partially Implantable Middle Ear Implant and the Indication", Advances in Audiology, Vol. 4, 160–166, Karger Basel, 1988; H. P. Zenner et al. "First implantations of a totally implantable electronic hearing system for sensorineural hearing loss", in HNO Vol. 46, 1998, pp. 844–852; H. Leysieffer et al. "A totally implantable hearing device for the treatment of sensorineural hearing loss: TICA LZ 3001", HNO Vol. 46, 1998, pp. 853–863; H. P. Zenner et al. "Active electronic hearing implants for patients with conductive and sensorineural hearing loss—a new era of ear surgery", HNO 45: 749–774; H. P. Zenner et al. "Totally implantable hearing device for sensorineural hearing loss", The Lancet Vol. 352, No. 9142, page 1751; and are described in numerous patent documents, thus among others in published European Patent Applications EP 0 263 254 A1, in European Patents EP 0 400 630 B1 and EP 0 499 940 B1 and in U.S. Pat. Nos. 3,557,775, 3,712,962, 3,764,748, 5,411,467, 4,352,960, 4,988,333, 5,015,224, 5,015,225, 5,360,388, 5,772,575, 5,814,095, 5,951,601, 5,977,689 and 5,984,859. Here the insertion of an electromechanical transducer through an opening in the promontory for direct fluid stimulation in the inner ear is described in U.S. Pat. Nos. 5,772,575, 5,951,601, 5,977,689 and 5,984,859.

Many patients with inner ear damage also suffer from temporary or permanent noise impressions (tinnitus) which cannot be surgically corrected and against which up to date there are no approved drug treatments. Therefore so-called tinnitus maskers (WO-A 90/07251, published European Patent Application EP 0 537 385 A1, German Utility Model No. 296 16 956) are known. These devices are small, battery-driven devices which are worn like a hearing aid behind or in the ear and which, by means of artificial sounds which are emitted via for example a hearing aid speaker into the auditory canal, psychoacoustically mask the tinnitus and thus reduce the disturbing noise impression if possible to below the threshold of perception. The artificial sounds are often narrow-band noise (for example, tierce noise) which can be adjusted in its spectral position and its loudness level via a programming device to enable adaptation to the individual tinnitus situation as optimum as possible. In addition, there since recently exists the so-called retraining method in which by combination of a mental training program and presentation of broadband sound (noise) near the auditory threshold in quiet the perceptibility of the tinnitus is likewise supposed to be largely suppressed (H. Knoer "Tinnitus retraining therapy and hearing acoustics" journal "Hoerakustik" February 1997, pages 26 and 27). These devices are also called "noisers".

In the two aforementioned methods for hardware treatment of tinnitus, hearing aid-like, technical devices must be carried visibly outside on the body in the area of the ear; they stigmatize the wearer and therefore are not willingly worn.

U.S. Pat. No. 5,795,287 describes an implantable tinnitus masker with direct drive of the middle ear for example via an electromechanical transducer coupled to the ossicular chain. This directly coupled transducer can preferably be a so-called "Floating Mass Transducer" (FMT). This FMT corresponds to the transducer for implantable hearing aids which is described in U.S. Pat. No. 5,624,376.

In commonly owned co-pending U.S. patent application Ser. Nos. 09/372,172 and 09/468,860 which are hereby incorporated by reference implantable systems for treatment of tinnitus by masking and/or noiser functions are described, in which the signal-processing electronic path of a partially or totally implantable hearing system is supplemented by corresponding electronic modules such that the signals necessary for tinnitus masking or noiser functions can be fed into the signal processing path of the hearing aid function and the pertinent signal parameters can be individually adapted by further electronic measures to the pathological requirements. This adaptability can be accomplished by the necessary setting data of the signal generation and feed electronics being stored or programmed by hardware and software in the same physical and logic data storage area of the implant system, and the feed of the masker or noiser signal into the audio path of the hearing implant can be controlled via the corresponding electronic actuators.

Depending on the desired function, implantable rehabilitation devices of the aforementioned type are comprised of several functional units, especially a sensor (microphone) which converts the incident airborne sound into an electrical signal, an electronic signal processing, amplification and implant control unit, an implantable electromechanical or electroacoustic transducer which converts the amplified and preprocessed sensor signals into mechanical or acoustic vibrations and sends them via suitable coupling mechanisms to the damaged middle and/or inner ear, or in the case of cochlear implants a cochlear stimulation electrode, and an electric power supply system which supplies the aforementioned modules. Furthermore, there can be an external unit which makes available electrical recharging energy to the implant when the implant-side power supply unit contains a rechargeable (secondary) battery. Especially advantageous devices and processes for charging of rechargeable implant batteries are described in commonly owned co-pending U.S. patent application Ser. No. 09/311,566 and in commonly owned U.S. Pat. No. 5,279,292 which are hereby incorporated by reference. Preferably there can also be a telemetry unit with which patient-specific, audiological data can be wirelessly transmitted bidirectionally or programmed in the implant and thus permanently stored, as was described by Leysieffer et al. in HNO Vol. 46, 1998, pp. 853–863.

Basically, in all these at least partially implantable systems the (audio) signal processing or signal generation and the implant control modules such as for example a controlled battery recharging system or a telemetry system for bidirectional transmission of for example variable, patient-specific parameters are accomplished on the implant-side by permanently fixed hardware units. This also applies when for signal processing or generation or for implant management digital signal processors or microcontrollers or microprocessors are used, regardless of whether they are built as so-called "hardwired logic", i.e. in "hardwired" logic architecture, or whether their operating programs are stored in read-only memory areas (for example, ROM) of the corresponding processors. These programs which are provided and are necessary for basic operation of the implant and for the intended functions are hereinafter called the operating program or the operating software. In the known implant systems this operating software is placed in the system during production for example by mask programming of processor storage areas and can no longer be changed after implantation.

In contrast thereto, patient-specific data such as for example audiological adaptation data or also variable implant system parameters (for example, a variable in one of the aforementioned software programs for control of battery recharging) herein are called operating parameters. In known totally implantable implant systems, after implantation these operating parameters can be transmitted transcutaneously, i.e. wirelessly through the closed skin, to the implant and thus can be changed.

The above described, at least partially implantable hearing systems for rehabilitation of a inner ear damage which are based on an output-side electromechanical transducer differ from conventional hearing aids essentially only in that the output-side acoustic stimulus (i.e. an amplified acoustic signal in front of the eardrum) is replaced by an amplified mechanical stimulus of the middle ear or inner ear. The acoustic stimulus of a conventional hearing aid ultimately leads to vibratory, i.e. mechanical stimulation of the inner ear, via mechanical stimulation of the eardrum and the subsequent middle ear. The requirements for effective audio signal preprocessing are fundamentally similar or the same. Furthermore, in both embodiments on the output side a localized vibratory stimulus is ultimately routed to the damaged inner ear (for example, an amplified mechanical vibration of the stapes in the oval window of the inner ear).

In cochlear implants exclusively electrical stimulation signals are used. After implantation of a CI for completely deaf patients generally training for rehabilitation of hearing is necessary since the artificial stimuli must be learned because fundamentally they do not correspond to the biologically proper form of stimulation of the inner ear. Conversely, this rehabilitation phase is eliminated after implantation of an electromechanical hearing system for the hard-of-hearing, since the mechanical stimulation form, as described above, is biologically suitable and, at least with respect to the basic function, ultimately corresponds to a large extent to treatment by a hearing aid, i.e. the stimulation at the entry to the inner ear is of vibratory nature.

Recently, partially and fully implantable hearing systems for rehabilitation of inner ear damage have been in clinical use. Depending on the physical principle of the output-side electromechanical transducer and especially its coupling type to the ossicle of the middle ear, it is to be seen that the attained results of improving speech comprehension can be very different. In addition, for many patients a sufficient loudness level cannot be reached. This aspect is spectrally very diverse; this can mean that for example at medium and high frequencies the generated loudness is sufficient, but not at low frequencies, or vice versa. Furthermore the spectral bandwidth which can be transmitted can be limited, thus for example for electromagnetic transducers to low and medium frequencies and for piezoelectric transducers to medium and high frequencies. In addition, nonlinear distortions which are especially pronounced in electromagnetic transducers can have an adverse effect on the resulting sound quality. The lack of loudness leads especially to the fact that the audiological indication range for implantation of an electromechanical hearing system can be very limited. This means that patients for example with sensorineural hearing loss of greater than 50 dB HL (hearing loss) in the low tone range can only be inadequately treated with a piezoelectric system. Conversely pronounced high tone losses can only be poorly treated with electromagnetic transducers.

For the aforementioned reasons, up to now implantable electromechanical systems cannot be employed for hearing disorders which approach deafness. Here cochlear implants with purely electrical stimulation of the inner ear may be considered which of course do not promise sound quality which for example would enable acceptable music transmission, but which rather are primarily designed for acquiring or restoring sufficient speech comprehension, as much as possible without lip reading. As a result of the electrical stimulation, as described, hearing losses which extend to complete deafness are possible in a spectrally wide audiological range.

Recently it has become scientifically known from CI implantations that even for incomplete deafness cochlear implants (CIs) can be successfully used when sufficient speech discrimination can no longer be achieved with a conventional hearing aid. Interestingly it was demonstrated that the important inner ear structures which enable residual acoustic hearing capacity can be maintained in part or largely stably over time when a CI electrode is inserted into the cochlea (S. Ruh et al.: "Cochlear implant for patients with residual hearing", Laryngo-Rhino-Otol. 76 (1997) 347–350; J. Mueller-Deile et al.: "Cochlear implant supply for non-deaf patients?" Laryngo-Rhino-Otol. 77 (1998) 136–143; E. Lehnhardt: "Intracochlear placement of cochlear implant electrodes in soft surgery technique", HNO 41 (1993), 356–359). In the foreseeable future it certainly will be possible, in case of residual hearing capacity, to clinically place CI electrodes intracochlearly in a manner such that the remaining inner ear structures can be preserved over the long term and thus can continue to be stimulated in a biologically proper manner, i.e. vibrationally, and lead to a usable hearing impression.

SUMMARY OF THE INVENTION

The primary object of the present invention is to devise an at least partially implantable system for rehabilitation of a hearing disorder which is improved with respect to the known systems described above and which can be adapted especially effectively and flexibly to the individual pathological and audiological situation of the respective patient.

In accordance with the invention this object is achieved in that, in an at least partially implantable system for rehabilitation of a hearing disorder which comprises at least one sensor (microphone) for picking up the acoustic signal and for conversion thereof into corresponding electrical signals, an electronic signal processing unit for audio signal processing and amplification, an electrical power supply unit which supplies energy to individual components of the system, and an output-side actory stimulation arrangement, by the output-side stimulation arrangement having in combination an electromechanical transducer for mechanical stimulation of the middle ear or inner ear and an intracochlear, electrically acting stimulation electrode array having at least one stimulation electrode for electrical stimulation of the inner ear are provided.

The present invention at least partially circumvents, on the one hand, the aforementioned disadvantages of currently available implantable electromechanical hearing systems and on the other hand the drawbacks of cochlear implants, by using both types of stimulation, i.e. mechanical stimulation and electrical stimulation, in a single implant system, which two types of stimulation, depending on the individual pathological and audiological situation, can be applied patient-specifically. This system can be called a "dual" hearing implant. Furthermore, by the use of the hearing implant system of the present invention tinnitus which can be localized at least peripherally will be more effectively masked than with known conventional tinnitus maskers.

The output-side electromechanical transducer is preferably made hermetically sealed, and basically, can operate according to any known electromechanical transducer principle, and can be designed especially as an electromagnetic, electrodynamic, piezoelectric, magnetostrictive or dielectric (capacitive) transducer. The piezoelectric principle and the dielectric or capacitive principle are especially preferred. When using the piezoelectric transducer principle they are advantageously made using lead zirconate titanate ceramics or PVDF (polyvinylidene fluoride).

The output-side electromechanical transducer can be designed for direct mechanical coupling to the middle ear or for contactless, air gap-coupled coupling to the middle ear according to the electromagnetic transducer principle (permanent magnet attached to the ossicle) in order to transmit its vibratory output stimulus to an ossicle of the middle ear.

However, the electromechanical transducer can also be designed for direct hydromechanical coupling to the inner ear, wherein transmission of the vibratory output stimulus to the inner ear can be effected by direct mechanical stimulation of the lymphatic inner ear spaces via a passage through the oval, the round or an artificial cochlear window. This direct stimulation of the cochlea has the advantage that the occurrence of feedback, i.e., coupling of the output signal into the sensor (microphone), is prevented or largely reduced because the ossicle chain and thus the eardrum are not excited to vibrations or only are excited to a reduced degree. This is especially advantageous when an acoustic sensor (microphone function) is applied in the immediate vicinity of the eardrum, as is known from U.S. Pat. Nos. 5,814,095 and 5,999,632.

The output-side electromechanical transducer preferably has a transmission range from about 100 Hz to about 10 kHz and it is preferably tuned high, i.e., their its mechanical resonant frequency is at the upper end of the desired transmission frequency range, especially at about 8 kHz to about 10 kHz. This results in that the deflection frequency response of the transducer in the transmission range is largely free of resonances and in the case of voltage impression and use of piezoelectric transducers, is flat regardless of frequency. Thus, there is no ripple in the transmission range.

The signal processing unit, preferably, has a preprocessing arrangement for pre-amplification and/or filtering and for analog-digital (A/D) conversion of the acoustic sensor signals. It can, in particular, comprise anti-aliasing filters. If a plurality of acoustic sensors are used, preferably each of the acoustic sensors has an analog-digital converter connected to the output thereof.

In another embodiment of the invention, the signal processing unit can contain software modules which, parallel to operation of the hearing aid, enables masking of tinnitus. With this dual hearing implant system, tinnitus which can be at least peripherally localized can be masked more effectively than with known convention tinnitus maskers.

The signal processing unit advantageously has a digital signal processor for processing the A/D-converted acoustic sensor signals which have been optionally preprocessed by means of the preprocessing arrangement and/or for generation of digital signals for tinnitus masking, wherein at least one digital-analog converter is associated to the output-side stimulation arrangement and wherein preferable the output-side electromechanical transducer and the electrode(s) of the stimulation electrode array have its own digital-analog converter connected to the output thereof.

In another embodiment of the invention, the digital signal processor contains software modules which control the output-side electromechanical transducer and the stimulation electrode array such that the spectral, time, amplitude- and phase-referenced transducer or stimulation electrode signal properties are configured such that optimum hearing success is achieved in a manner specific to the patient.

The software modules can be designed to be static such that as a result of scientific findings they are stored once in a program storage of the digital signal processor and remain unchanged. But, if later, for example, due to more recent scientific findings, improved algorithms for speech signal conditioning and processing are available and are desired to be used, the entire implant or implant module which contains the corresponding signal processing unit must be replaced by a new unit with the altered operating software by invasive surgery on the patient. This surgery entails renewed medical risks for the patient and is very complex.

This problem can be solved in that, in another embodiment of the invention, a wireless, preferably PC-based telemetry means is provided for transmission of data between the implanted part of the system and an external unit, especially an external programming system, preferably a rewritable implantable storage arrangement being assigned to the signal processor for storage and retrieval of the operating program, and at least parts of the operating program can be replaced or changed by data transmitted from the external unit via the telemetry means. In this way, after implantation of the implantable system the operating software as such can be changed or even completely replaced, as is explained for otherwise known systems for rehabilitation of hearing disorders in commonly owned U.S. Pat. No. 6,198,971 which is hereby incorporated by reference.

In addition, the design of totally implantable systems preferably is such that in a manner known per se, after implantation also operating parameters, i.e., patient-specific data, for example, audiological adaption data, or variable implant system parameters (for example, a variable in a software program for control of battery recharging), can be transmitted transcutaneously, i.e. wirelessly through the closed skin, to the implant and can thus be changed. In such a case, the software modules are designed to be preferably dynamic, or in other words, adaptive, in order to rehabilitate the hearing disorder as optimally as possible. In particular, the software modules can be designed to be adaptive, and parameter matching can be done by training by the implant wearer and using other aids.

Furthermore, the signal processing electronics can contain a software module which achieves stimulation as optimum as possible based on an adaptive neural network. Training of this neural network can take place again by the implant wearer and/or using other external aids.

The storage arrangement for storage of operating parameters and the storage arrangement for storage and retrieval of the operating program can be implemented as storages independent of one another; however there can also be a single storage in which both the operating parameters and also operating programs can be filed.

This approach allows matching of the system to circumstances which can be detected only after implantation of the implantable system. Thus, for example, in an at least partially implantable hearing system for rehabilitation of a monaural or binaural inner ear disorder and of a tinnitus by mechanical stimulation of the inner ear, the sensoric (acoustic sensor or microphone) and actoric (output stimulator) biological interfaces are always dependent on anatomic, biological and neurophysiological circumstances, for example on the interindividual healing process. These interface parameters can also be individual, also especially time-variant. Thus, for example the transmission behavior of an implanted microphone can vary interindividually and individually as a result of being covered by tissue, and the transmission behavior of an electromechanical transducer which is coupled to the inner ear can vary in view of on different coupling qualities. These differences of interface parameters which cannot be eliminated or reduced in the devices known from the prior art even by replacing the implant can now be optimized by changing or improving the signal processing of the implant.

In an at least partially implantable hearing system, it can be advisable or become necessary to implement signal processing algorithms which have been improved after implantation. Especially the following should be mentioned here.

speech analysis processes (for example, optimization of a fast Fourier transform (FFT))

static or adaptive noise detection processes static or adaptive noise suppression processes processes for optimization of the signal to noise ratio within the system optimized signal processing strategies in progressive hearing disorder output level-limiting processes for protection of the patient in case of implant malfunctions or external faulty programming processes of preprocessing of several sensor (microphone) signals, especially for binaural positioning of the sensors processes for binaural processing of two or more sensor signals in binaural sensor positioning, for example optimization of spacial hearing or spacial orientation phase or group delay time optimization in binaural signal processing processes for optimized driving of the output stimulators, especially for binaural positioning of the stimulators.

Among others, the following signal processing algorithms can be implemented with this system even after implantation:

processes for feedback suppression or reduction processes for optimization of the operating behavior of the output transducer(s) (for example, optimization of the frequency response and phase response, improvement of the impulse response)

speech signal compression processes for sensorineural hearing loss signal processing methods for recruitment compensation in sensorineural hearing loss Furthermore, in implant systems with a secondary power supply unit, i.e., a rechargeable battery system, but also in systems with primary battery supply, it can be assumed that these electrical power storages will enable longer and longer service lives, and thus, increasing residence times in the patients as technology advances. It can be assumed that fundamental and applied research for signal processing algorithms will make rapid progress. The necessity or the desire for operating software adaptation and modification will therefore presumably take place before the service life of the implanted power source expires. The system described here allows this adaptation of the operating programs of the implant even when it has already been implanted.

Preferably, there can furthermore be provided a buffer storage arrangement in which data transmitted from the external unit via the telemetry means can be buffered before being relayed to the signal processor. In this way, the transmission process from the external unit to the implanted system can be terminated before the data transmitted via the telemetry means are relayed to the signal processor.

Furthermore, there can be provided checking logic which checks the data stored in the buffer storage arrangement before relaying the data to the signal processor. There can be provided a microprocessor module, especially a microcontroller, for control of the A/D-converters and/or the D/A converters and/or the signal processor within the implant via a data bus, preferably the checking logic and the buffer storage arrangement being implemented in the microprocessor module, and wherein also program parts or entire software modules can be transferred via the data bus and the telemetry means between the outside world, the microprocessor module and the signal processor.

An implantable storage arrangement for storing the working program for the microprocessor module is preferably assigned to the microprocessor module, and at least parts of the working program for the microprocessor module can be changed or replaced by data transmitted from the external unit via the telemetry means.

In another embodiment of the invention, at least two storage areas for storage and retrieval of at least the operating program of the signal processor may be provided. This contributes to the reliability of the system, in that due to the multiple presence of a storage area which contains the operating program(s), for example, after transmission from the exterior or when the implant is turned on, checking for the absence of faults in the software can be done.

Analogously to the above, the buffer storage arrangement can also comprise at least two storage areas for storage and retrieval of data transferred from the external unit via the telemetry means, so that after data transmission from the external unit still in the area of the buffer storage the absence of errors in the transferred data can be checked. The storage areas can be designed for example for complementary filing of the data transferred from the external unit. At least one of the storage areas of the buffer storage arrangement however can also be designed to store only part of the data transferred from the external unit, wherein in this case the absence of errors in the transferred data is checked in sections.

Furthermore, to ensure that in case of transmission errors, a new transmission process can be started, a preprogrammed read-only memory area which cannot be overwritten can be assigned to the signal processor, in which ROM area the instructions and parameters necessary for "minimum operation" of the system are stored, for example, instructions which after a "system crash" ensure at least error-free operation of the telemetry means for receiving an operating program and instructions for its storage in the control logic.

As already mentioned, the telemetry means is advantageously designed not only for reception of operating programs from the external unit but also for transfer of operating parameters between the implantable part of the system and the external unit such that on the one hand such parameters (for example the volume) can be adjusted by a physician, a hearing aid acoustics specialist or the wearer of the system himself, and on the other hand, the system can also transfer the parameters to the external unit, for example, to check the status of the system.

A totally implantable hearing system of the aforementioned type can have, on the implant side, in addition to the actoric stimulation arrangement and the signal processing unit, at least one implantable acoustic sensor and a rechargeable electrical storage element, and in this case, a wireless transcutaneous charging device can be provided for charging of the storage element. It goes without saying that, for power supply, there can also be provided a primary cell or another power supply unit which does not require transcutaneous recharging. This applies especially when it is considered that, in the near future, mainly by continuing development of processor technology a major reduction in power consumption for electronic signal processing can be expected so that for implantable hearing systems new forms of power supply will become usable in practice, for example, power supply which uses the Seebeck effect, as is described in U.S. Pat. No. 6,131,581. Preferably, there is also provided a wireless remote control for control of the implant functions by the implant wearer.

In case of a partially implantable hearing system, at least one acoustic sensor, an electronic signal processing arrangement, a power supply unit and a modulator/transmitter unit are contained in an external module which can be worn outside on the body, especially on the head over the implant. The implant comprises the output-side electro-mechanical transducer and the intracochlear stimulation electrode array, but is passive in terms of energy and receives its operating energy and transducer control data via the modulator/transmitter unit in the external module.

The described system can be designed to be monaural or binaural for the fully implantable design as well as for the partially implantable design. A binaural system for rehabilitation of a hearing disorder of both ears has two system units which each are assigned to one of the two ears. In doing so the two system units can be essentially identical to one another. However, one of the system units can also be designed as a master unit and the other system unit as a slave unit which is controlled by the master unit. The signal processing modules of the two system units can communicate with one another in any way, especially via a wired implantable line connection or via a wireless connection, preferably a bidirectional high frequency path, a ultrasonic path coupled by bone conduction, or a data transmission path which uses the electrical conductivity of the tissue of the implant wearer such that in both system units optimized binaural signal processing and transducer array control are achieved.

These and further objects, features and advantages of the present invention will become apparent from the following description when taken in connection with the accompanying drawings which, for purposes of illustration only, shows several embodiments in accordance with the present invention.

DETAILED DESCRIPTION OF THE INVENTION

Figure 1:
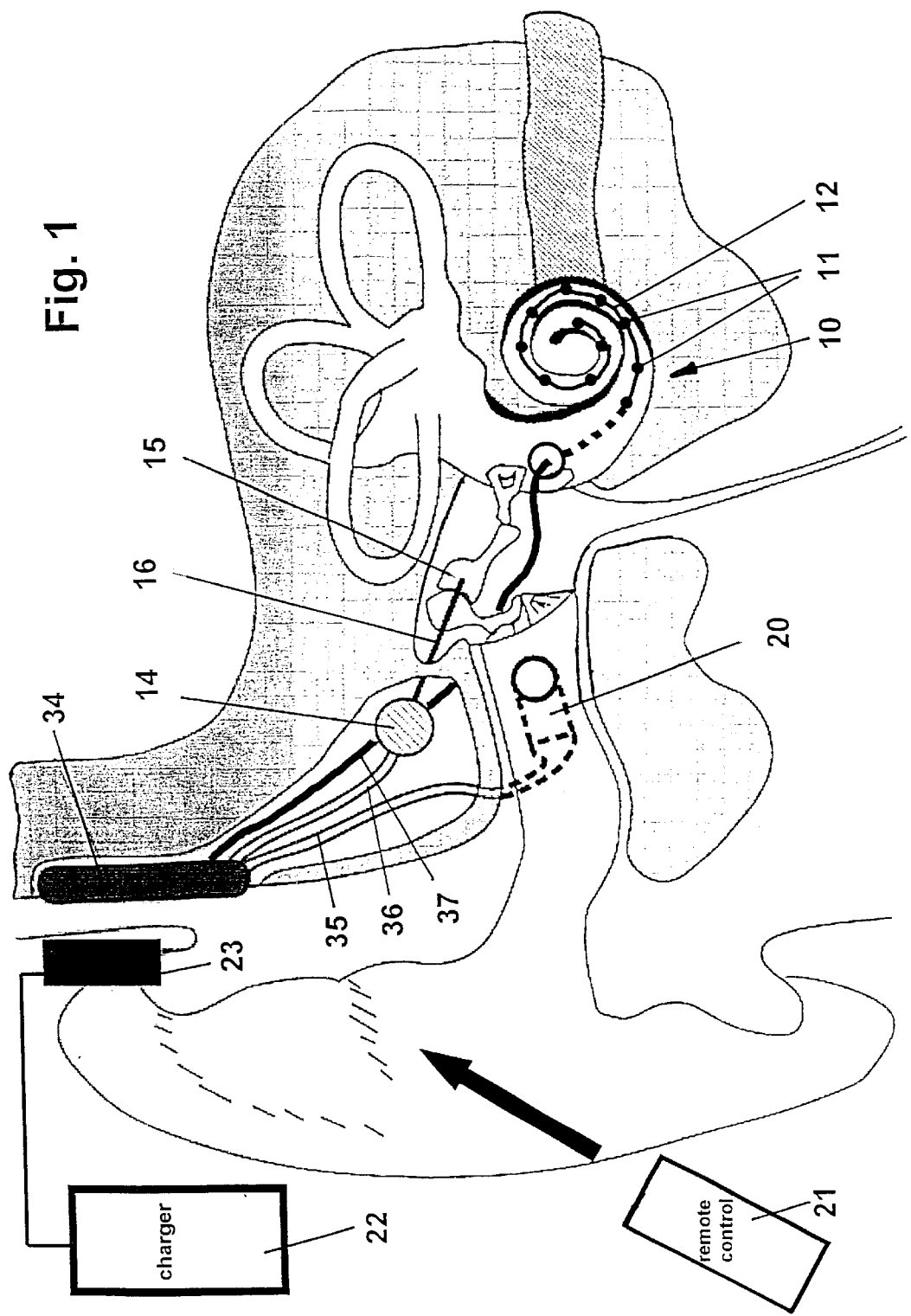
FIG. 1 schematically shows an embodiment for the structure of a totally implantable dual hearing system in accordance with the invention.

FIG. 1 schematically shows the structure of a totally implantable hearing system, an output-side actory stimulation arrangement of which comprises an electrical intracochlear array 10 having several stimulation electrodes 11 and an electromechanical transducer 14 which is coupled here, for example, to the incus 15.

The intracochlear stimulation electrode array 10 can be built, for example, as a unipolar or bipolar arrangement in any manner known for cochlear implants. It comprises an electrode carrier 12 of electrically insulating, flexible material along which the stimulation electrodes 11 connected to feed lines 13 are distributed at a distance to each other. The stimulation electrodes 11 are embedded in the carrier 12 or fixed on the carrier 12 such that a portion of the surface per stimulation electrode is in direct galvanic contact with the lymphatic fluid of the inner ear or directly with one of the neural structures to be stimulated.

The transducer 14 can be built, especially in the manner known from commonly owned U.S. Pat. No. 5,277,694 which is hereby incorporated by reference, such that a housing wall of a hermetically tight transducer housing is designed as a vibrating membrane which, together with a piezoelectric ceramic wafer applied to the inside thereof, comprises an electromechanically active heteromorph composite element, the mechanical vibrations of which are transmitted to the ossicular chain via a coupling rod 16 which is permanently attached to the outside of the membrane and optionally via a coupling element which is connected to the coupling rod. This transducer can be modified in the manner explained in commonly owned U.S. Pat. No. 6,123,660 which is hereby incorporated by reference, such that, on the inside of the piezoelectric ceramic wafer, a permanent magnet is attached which interacts with an electromagnetic coil, such as an electromagnetic transducer. Such a combined piezoelectric-electromagnetic transducer is advantageous in particular with respect to a wide frequency band and achieving relatively high vibration amplitudes with comparatively small supplied energy.

The transducer 14 can be an electromagnetic transducer arrangement as is described in commonly owned U.S. Pat. No. 6,162,169 which is hereby incorporated by reference, i.e. a transducer arrangement which is provided with a housing which can be fixed at the implantation site with reference to the skull and a mechanically stiff coupling element which can move relative to the housing, and in which in the housing there is an electromechanical transducer by means of which the coupling element can be caused to vibrate, and which is designed as an electromagnet arrangement which has a component which is fixed relative to the housing and a vibrating component which is connected to the coupling element such that the vibrations of the vibrating component are transmitted to the coupling element.

To couple the electromechanical transducer to the middle ear or inner ear, especially coupling arrangements as disclosed in U.S. Pat. No. 5,941,814 are suited in which a coupling element, besides the coupling part for the pertinent coupling site, has a crimp sleeve which is first slipped loosely onto a rod-shaped part of the coupling rod which is provided with a rough surface and which is connected to the transducer in the aforementioned manner. During implantation the crimp sleeve can simply be pushed and turned relative to the coupling rod to exactly align the coupling part of the coupling element with the intended coupling site. Then the crimp sleeve is fixed by its being plastically cold-deformed by means of a crimping tool. Alternatively, the coupling element can be fixed with reference to the coupling rod also by means of a belt loop which can be tightened.

Other coupling arrangements which can be preferably used here are described, in particular, in commonly owned co-pending U.S. patent application Ser. Nos. 09/576,009, 09/626,745, 09/613,560, 09/680,489 and 09/680,488 which are hereby incorporated by reference. Thus, according to U.S. patent application Ser. No. 09/576,009, the coupling element, at its coupling end, can have a contact surface which has a surface shape which is matched or can be matched to the surface shape of the coupling side, and has a surface composition and surface size such that by placing the coupling end against the coupling site a dynamic tension-compression force coupling between coupling element and ossicular chain is achieved due to surface adhesion which is sufficient for secure mutual connection of the coupling element and the ossicular chain. The coupling element can be provided with an attenuation element which adjoins the coupling site in the implanted state, and which has entropy-elastic properties in order to achieve an optimum form of vibration of the footplate of the stapes or the membrane which closes the round window or an artificial window in the cochlea, in the vestibulum or in the labyrinth and to minimize the risk of damage to the natural structures in the area of the coupling site during and after implantation (U.S. patent application Ser. No. 09/626,745).

The coupling element according to above-incorporated U.S. patent application Ser. No. 09/613,560 can be provided with an operating device for selectively moving the coupling element between an open position in which the coupling element can engage and disengage the coupling site, and a closed position in which the coupling element in the implanted state is connected by force-fit and/or form-fit to the coupling site.

For mechanical coupling of the electromechanical transducer to a preselected coupling site on the ossicular chain, the footplate of the stapes or a membrane which closes the round window or an artificial window in the cochlea, in the vestibulum or in the labyrinth (equilibrium organ) also a coupling arrangement (above-incorporated U.S. patent application Ser. No. 09/680,489) may be used which has a coupling rod which can be caused by the transducer to mechanically vibrate, and a coupling element which can be connected to the preselected coupling site, the coupling rod and the coupling element being interconnected by at least one coupling and at least one section of the coupling element which in the implanted state abuts the coupling site being designed for low-loss delivery of vibrations to the coupling site, said coupling comprising a first coupling half with an approximately spherical outside contour, and a second coupling half that is adapted to receive said spherical outside contour of said first coupling half and having an inside contour that is at least partly complementary to said spherical outside contour of said first coupling half, wherein said coupling is adapted to be substantially rigid with respect to dynamic forces which occur when said hearing system is implanted, and adapted to reversibly swivel or turn against friction forces, when the hearing system is implanted or adjusted. According to a modified embodiment of such a coupling arrangement (above-incorporated U.S. patent application Ser. No. 09/680,488), the first half of the coupling has an outer contour with an at least approximately cylindrical, preferably circularly cylindrical, shape which can be accommodated in the inner contour of a second coupling half, which inner contour is at least partially complementary to the outer contour, wherein a section of the coupling element which abuts the coupling site in the implanted state is designed for low-loss delivery of vibrations to the coupling site, wherein in the implanted state, transmission of dynamic forces between the two halves of the coupling takes place essentially in the direction of the longitudinal axis of the first coupling half, and wherein the coupling can be reversibly coupled and decoupled, and can be reversibly moved linearly and/or rotationally with reference to the longitudinal axis of the first coupling half, but is rigid to dynamic forces which occur in the implanted state.

The totally implantable hearing system shown in FIG. 1 also includes an implantable microphone 20, a wireless remote control 21 for controlling the implant functions by the implant wearer, and a wireless, transcutaneous charging system comprising a charging device 22 and a charging coil 23 for recharging of a secondary battery 25 (FIG. 2) located in the implant for power supply of the hearing system.

The microphone 20 can advantageously be built in the manner known from commonly owned U.S. Pat. No. 5,814,095, which is hereby incorporated by reference, and can be provided with a microphone capsule which is accommodated hermetically sealed on all sides within a housing, and with an electrical lead-through wire connector for routing at least one electrical connection from within the housing to outside thereof, wherein the housing has at least two legs, which are arranged at an angle relative to one another, a first of said legs containing the microphone capsule and being provided with a sound inlet membrane, and a second of said legs containing the electrical lead-through wire connector and being set back relative to the plane of the sound inlet membrane, and wherein the geometry of the microphone housing is chosen such that when the microphone is implanted in the mastoid cavity the leg which contains the sound inlet membrane projects from the mastoid into an artificial hole in the posterior bony wall of the auditory canal and the sound inlet membrane touches the skin of the wall of the auditory canal.

To fix the implanted microphone 20, there can preferably be a fixation element of the type known from U.S. Pat. No. 5,999,632 which has a sleeve, a cylindrical housing part of which surrounds the leg which contains the sound inlet membrane, wherein the sleeve is provided with projecting, elastic flange parts which can be placed against the side of the wall of the auditory canal facing the skin of the auditory canal. The fixation element preferably comprises a holding device which, before implantation, maintains the flange parts mentioned above, against the elastic restoration force of the flange parts, in a bent position which allows insertion through the hole of the wall of the auditory canal.

Figure 2:
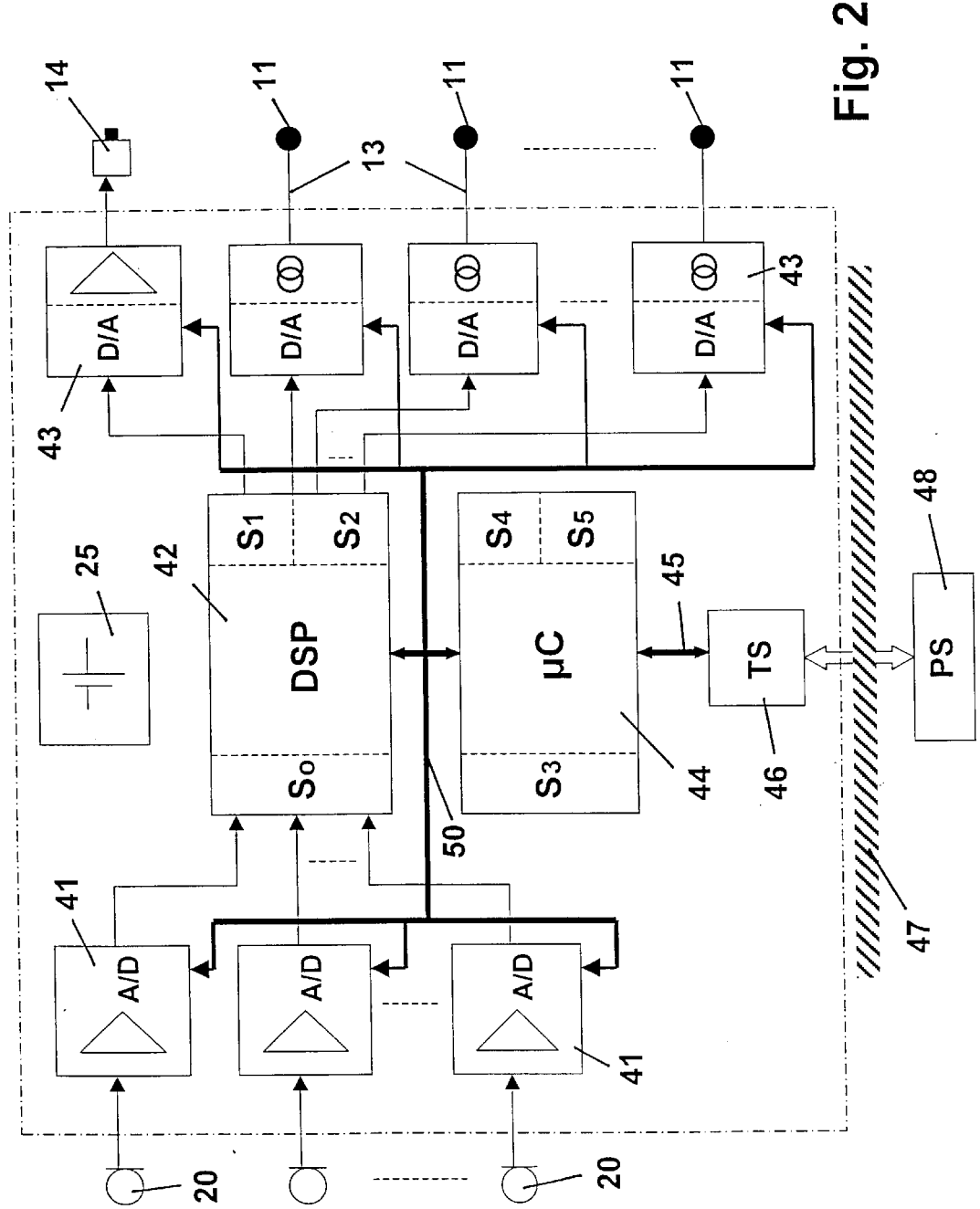
FIG. 2 schematically shows one embodiment for the structure of a signal processing electronic module of an at least partially implantable hearing system.

The charging coil 23 which is connected to the output of the charging device 22, preferably in the manner known from U.S. Pat. No. 5,279,292, forms part of a transmitting serial resonant circuit which can be inductively coupled to a receiving serial resonant circuit which is not shown. The receiving serial resonant circuit can be part of an implantable electronic module 34 (FIG. 2) and according to U.S. Pat. No. 5,279,292 can form a constant current source for the battery 25 (FIG. 2). Here, the receiving serial resonant circuit is connected into a battery charging circuit which depending on the respective phase of the charging current flowing in the charging circuit is closed via one branch or the other of a full wave rectifier bridge.

In the arrangement shown in FIG. 1, the electronic module 34 is connected via a microphone line 35 to the microphone 40, via the transducer feed line 36 to the electromechanical transducer 14 and via an array feed line 37 to the intracochlear stimulation electrode array 10.

FIG. 2 shows the possible structure of the signal processing electronic module 34 of an at least partially implantable hearing system. The external acoustic signal is picked up via one or more acoustic sensors (microphones) 20 and is converted into electrical signals. The analog electrical sensor signals are routed to modules 41 in which they are preprocessed, especially preamplified, and converted into digital signals (A/D). This preprocessing can provided by, for example, analog linear or nonlinear pre-amplification and filtering (for example, anti-aliasing filtration).

The digitized sensor signals are further processed in a digital signal processor 42 (DSP). The signal processor 42 contains a read-only-memory area SO which cannot be overwritten, in which the instructions and parameters necessary for "minimum operation" of the system are stored, and storage areas S1 and S2 in which the operating software of the intended function or functions of the implant system are stored. The rewriteable program storages S1 and S2 for storing the operating software can be based on EEPROM or on static RAM cells, and in the latter case, provisions should be made for this RAM area to always be "buffered" by the power supply system within the implant.

The digital output signals of the signal processor 42 are converted in digital-analog converters (D/A) 43 into analog signals and amplified and then supplied to the stimulating electrodes 11 and the output-side electromechanical transducer 14.

The signal processor 42 executes the intended function of the hearing implant. This includes audio signal processing for rehabilitation of a hearing disorder and optionally also signal generation in the case of a system with additional tinnitus masker or noiser function. Furthermore, the digital signal processor 42 contains software modules which provide for dual control of the stimulating electrode array 10 and the electromechanical transducer 14 in such a manner that the spectral, time, amplitude- and phase-referenced transducer or stimulating electrode signal properties are configured such that optimum hearing success is achieved for the pertinent patient. These software modules can be designed to be static and dynamic. A static design is intended to mean that the software modules, based on scientific findings, are stored once in the program storage of the signal processor 42 and remain unchanged. Dynamic means that these software modules are "able to learn", in order to approach as optimally as possible the desired hearing result in a time iterative manner. This means that the software modules can be designed to be adaptive, and parameter matching is done by training by the implant wearer and optionally using other aids such as rehabilitation programs. Furthermore, a software module can be provided which approximates hearing supply as optimum as possible based on an adaptive neural network. Training of this neural network can take place again by the implant wearer and/or using other external aids.

In order to also post-operatively implement the described software-based algorithms for a dual stimulation of the damaged hearing especially in a total implant that is as optimum as possible, the system shown in FIG. 2 contains a further microprocessor module, for example, a microcontroller (μC) 44 with the associated storages (S3, S4, S5). The storage S3 is a rewriteable storage in which an operating program for the microcontroller 44 is stored. Especially the operating software portions of the implant management system (for example, administration, monitoring and telemetry functions) can be stored in the storage areas S4 and S5. Storages S1 and/or S2 and/or S4 and/or S5 can also store patient-specific, for example audiological adaptation parameters which can be altered from the outside.

On the one hand, the microcontroller 44 communicates via a bidirectional data bus 45 and a telemetry system (TS) 46 wirelessly (for example, via inductive coupling) through the closed skin indicated at 47 with an external programming system (PS) 48. The programming system 48 can be a PC-based system with corresponding programming, processing, display and administration software. Via this telemetry interface, the operating software of the implant system which is to be changed or completely replaced is transmitted and at first buffered in the storage area S4 and/or S5 of the microcontroller 44. Thus, for example, simple verification of software transmission can be done by a reading process via the telemetry interface before the operating software or the corresponding signal processing portions of this software are transmitted into the program storage areas S1 and S2 of the digital signal processor 42 via a data bus 50. Furthermore, the working program for the microcontroller 44 can be changed or replaced in whole or in part via the telemetry interface using the external unit 48.

On the other hand, the microcontroller 44 controls within the implant, via the bidirectional data bus 50, the A/D converters 41 of the sensor preprocessing, the D/A converters 43 for control of the stimulating electrodes 11 and of the electromechanical transducer 14 and the signal processor 42 itself. The D/A converters 43 can also be partially or entirely omitted when there are digitally controlled power sources for the stimulating electrodes and/or, in case an electromagnetic output transducer 14 is used, for example, a pulse width-modulated serial digital output signal of the signal processor 42 is transmitted directly to the transducer 14. Via the data bus 50, program parts or entire software modules can also be transferred between an external unit, the microcontroller 44 and the signal processor 42.

In totally implanted embodiments, the implant system also contains a primary or secondary battery cell 25 which supplies the individual modules with electrical operating energy and which is preferably combined with the electronic module 34.

Figure 3:
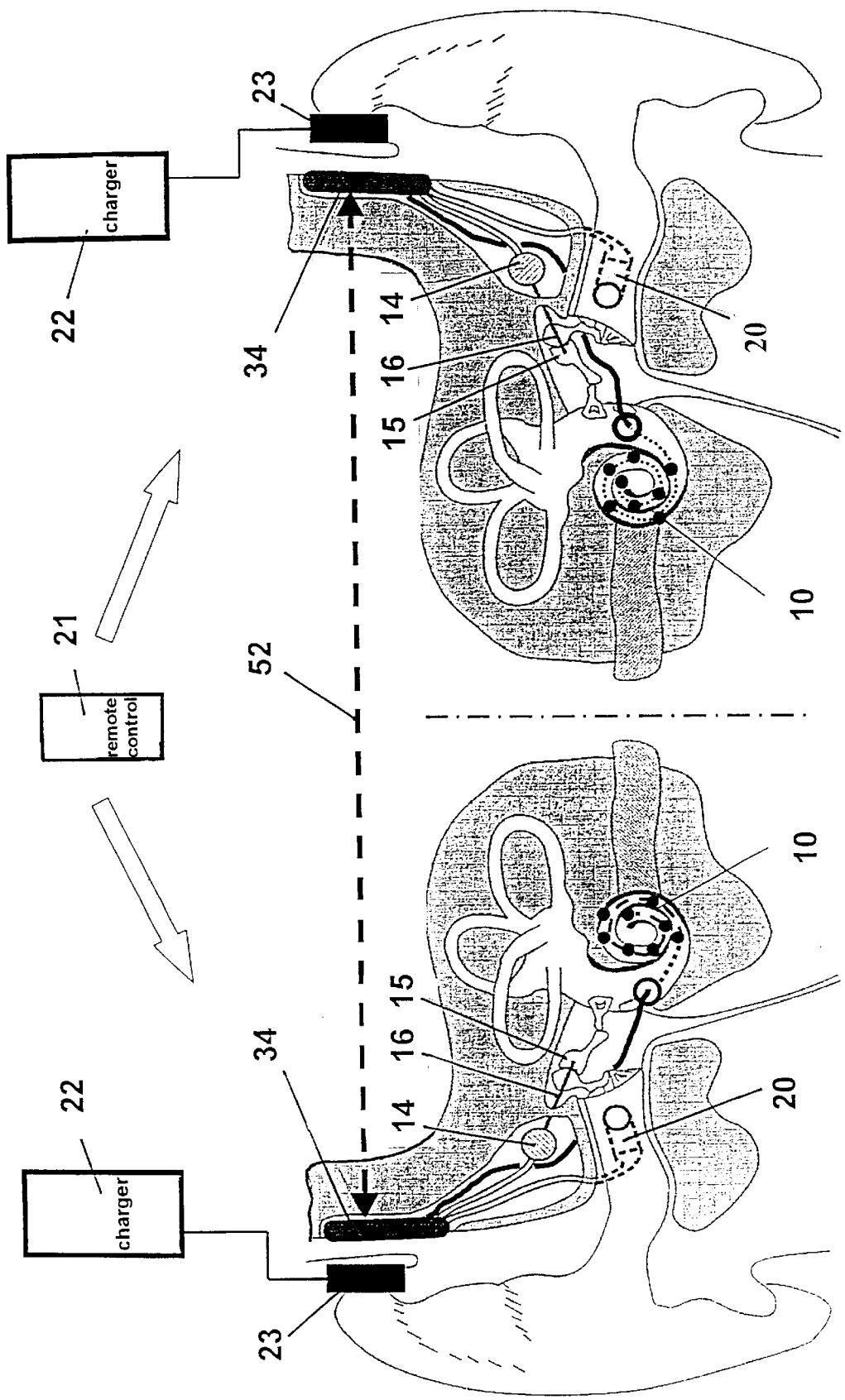
FIG. 3 shows a binaural application of a hearing implant as shown in FIG. 1 in which the signal processing modules communicate with one another via a wired implantable line connection.

FIG. 3 shows a binaural application of the hearing implant shown in FIG. 1. Here the signal processing modules 34 communicate with one another via a wired implantable line connection 52 such that optimum binaural signal processing and transducer or stimulation electrode array control is attained in both inner ears provided with implants. Furthermore, in this case, too, transcutaneous charging devices 22, 23 (not shown) are provided if secondary energy storage elements (batteries 25) are included in the implant, as well as a wireless remote control 21 for use by the implant wearer which synchronously controls the two electronic modules 34.

Figure 4:
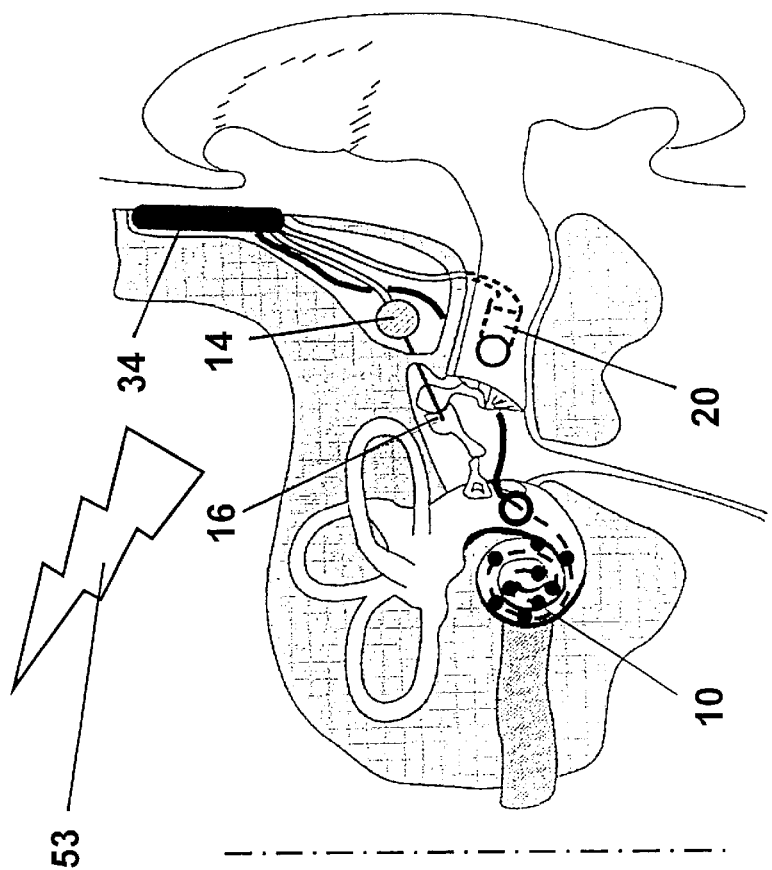
FIG. 4 shows a binaural application of a hearing implant as shown in FIG. 1 in which the signal processing modules communicate with one another via a wireless connection.
Figure 4:
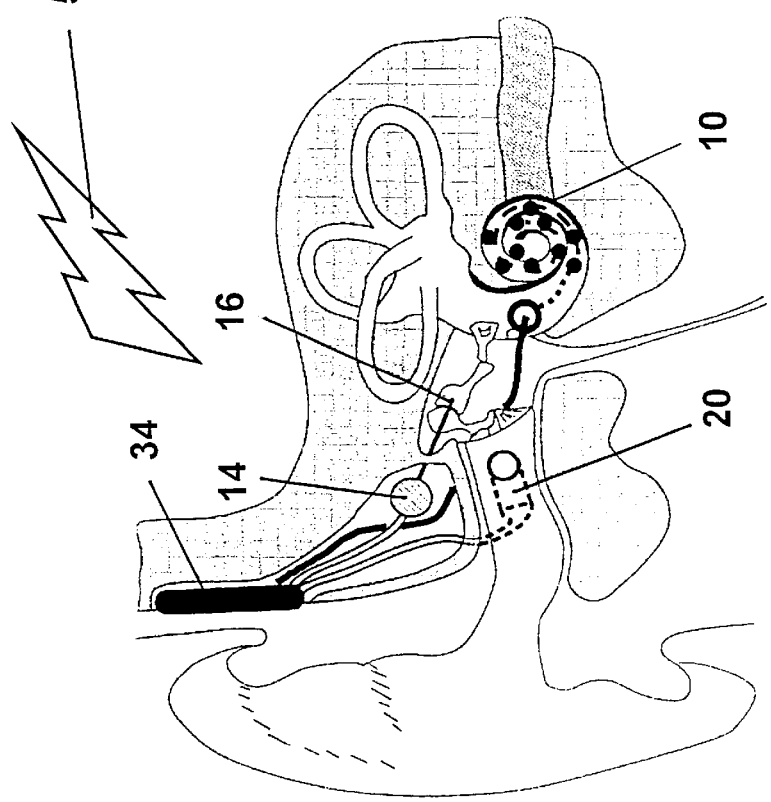

FIG. 4 shows the binaural application of a hearing implant according to FIG. 1 in which the signal processing modules 34 communicate with one another via a wireless connection (for example, a bidirectional high frequency path indicated at 53) such that optimum binaural signal processing and transducer or stimulation electrode array control is attained in both inner ears provided with implants. In this case too, there are provided transcutaneous charging devices 22, 23 (not shown) for the case of implant-side secondary energy storage elements (batteries 25) and a wireless remote control 21 for use by the implant wearer which synchronously controls the two electronic modules 34.

Figure 5:
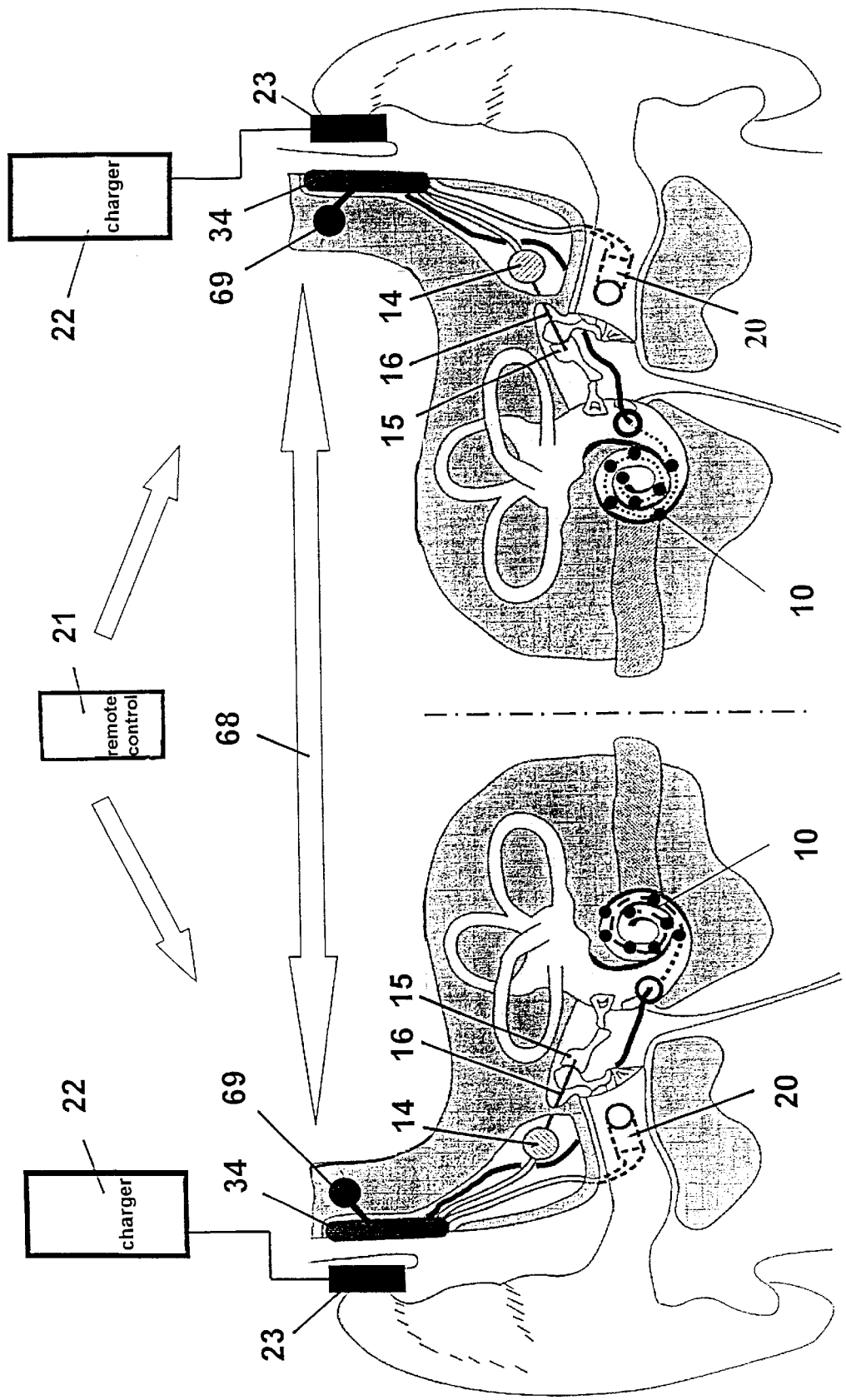
FIG. 5 shows a binaural application of a hearing implant as shown in FIG. 1 in which the signal processing modules communicate with one another via an ultrasonic path coupled by bone conduction.

The binaural embodiment of the hearing implant shown in FIG. 5 differs from that of FIG. 4 only in that, for wireless communication between the signal processing modules 34 of the two system units, there is an ultrasonic path 54 including ultrasonic couplers 55 which are coupled by bone conduction. In this case, the, for example digital, bidirectional information is preferably amplitude modulated or frequency modulated onto a carrier in the ultrasonic range The ultrasonic couplers 55 can be, as shown in FIG. 5, ultrasonic transmitters and receivers which are locally separated from the electronic module 34, which are connected via electrical lines, and which are preferably coupled securely in the mastoid area to the skull bone. The ultrasonic couplers however can also be integrated in the electronic modules 34 (not shown) when the electronic modules are implanted in the mastoid area such that ultrasonic conduction can take place through the skull bone.

Figure 6:
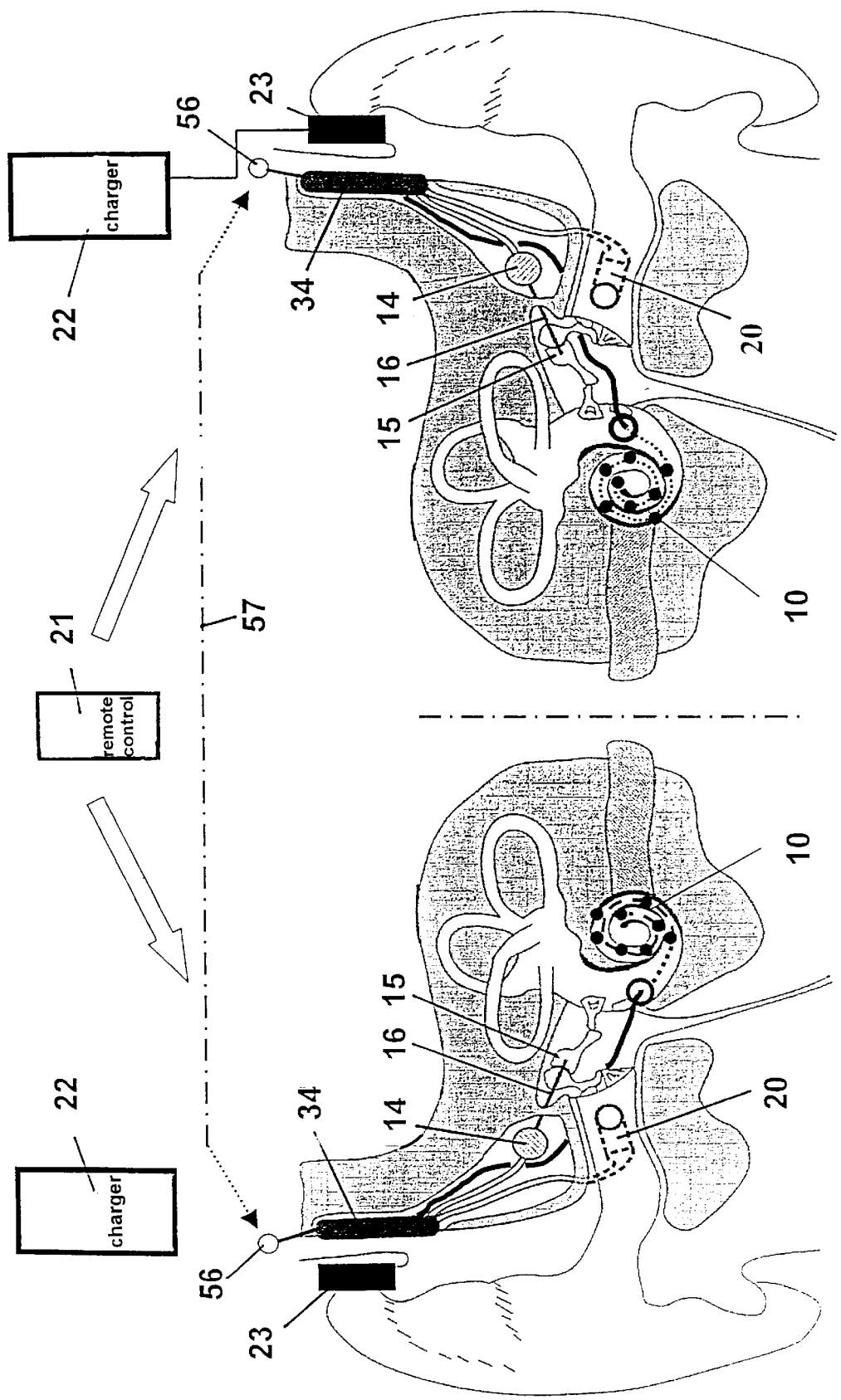
FIG. 6 shows a binaural application of a hearing implant as shown in FIG. 1 in which the signal processing modules communicate with one another via a transmission path which includes the tissue of the implant wearer, and FIG. 7 schematically shows one embodiment for the structure of a partially implantable hearing system with a stimulation arrangement as shown in FIG. 1.

A further modified embodiment of a binaurally designed hearing implant is shown in FIG. 6. In this embodiment, different from the embodiments of FIGS. 3 to 5, the, for example, digital, bidirectional information is preferably amplitude modulated or frequency modulated on the implant side onto a carrier and applied to the implanted electrodes 56 which are part of a data transmission path 57 which leads through the body tissue of the implant wearer. Thus, a modulated tissue current is obtained which in a manner known per se (German Patent Application DE-A-38 31 809) provides for the desired communication between the signal processing modules 34 of the two system units.

Figure 7:
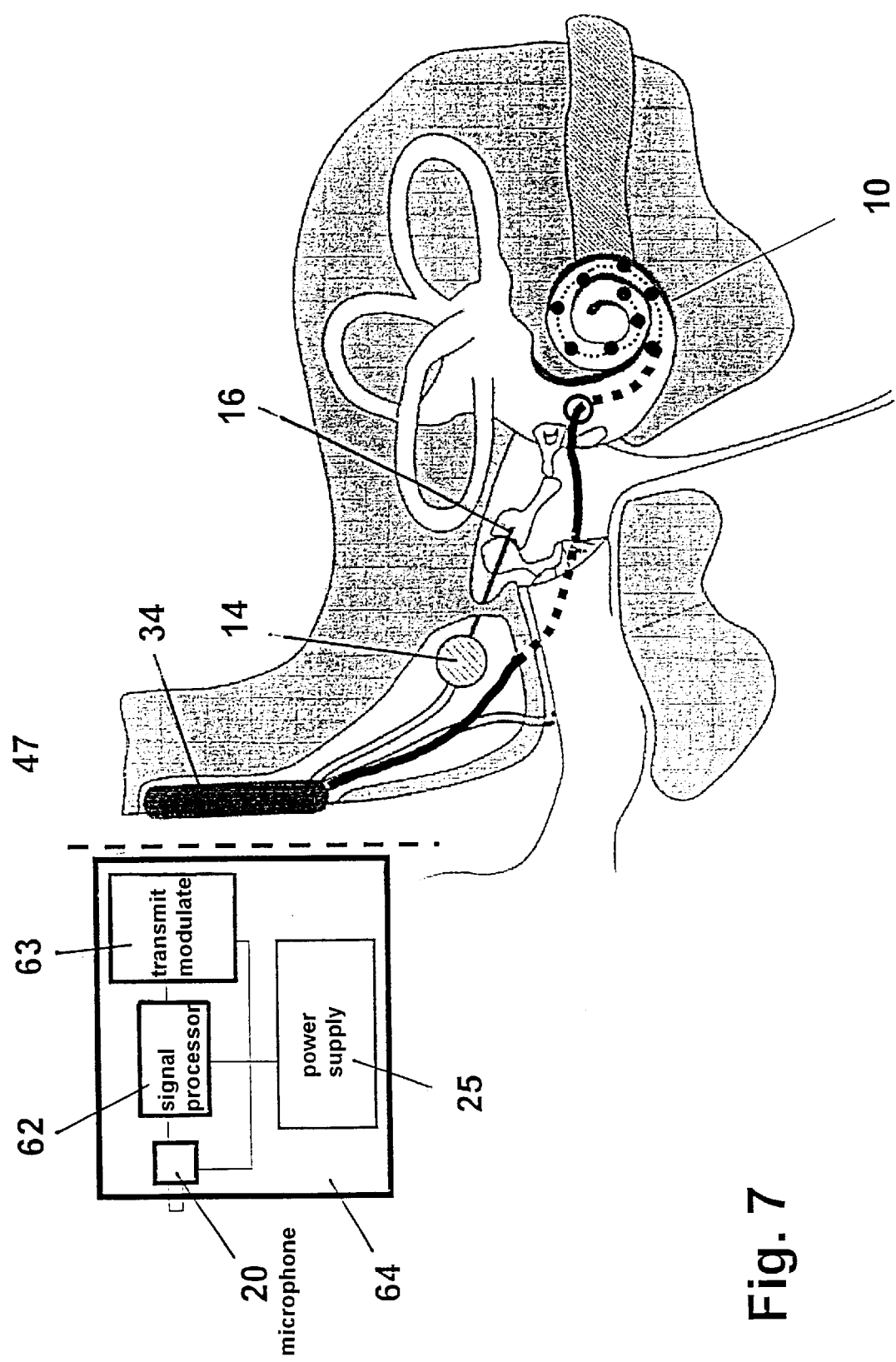

FIG. 7 schematically shows the structure of a partially implantable hearing system comprising an intracochlear stimulation electrode array 10 and an electromechanical transducer 14 as shown in FIG. 1. In this partially implantable system, a microphone 20, an electronic module 62 for electronic signal processing for the most part according to FIG. 2 (but without the telemetry system 46), the power supply (battery) 25 and a modulator/transmitter unit 63 are contained in an external module 64 which is to be worn externally on the body, preferably on the head over the implant. As in the known partial implants, the implant is passive in terms of energy. Its electronic module 34' (without the battery 52) receives its operating energy and transducer or stimulating electrode control data via the modulator/transmitter unit 63 in the external part 64

It goes without saying that a partially implantable system can also be binaurally applied, and that then, provisions can be made for communication between the two system units preferably according to the embodiments of binaural applications of fully implantable systems which are shown in FIGS. 3 to 6.

While a several embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

We claim:

1. At least partially implantable system for rehabilitation of a hearing disorder, comprising:
   at least one sensor for picking up an acoustic signal and converting it into corresponding electrical signals;
   an electronic signal processing unit for audio signal processing and amplification;
   an electrical power supply unit which supplies individual components of the system with energy; and
   an output-side actory stimulation arrangement;
   wherein said output-side actory stimulation arrangement has an electromechanical transducer for mechanical stimulation of the middle ear and an intracochlear, electrically acting stimulation electrode array with at least one stimulation electrode for electrical stimulation of the inner ear.

2. System as claimed in claim 1, wherein the electromechanical transducer is a transducer selected from the group consisting of electromagnetic, electrodynamic, piezoelectric, magnetostrictive or dielectric transducers.

3. System as claimed in claim 1, wherein the output-side electromechanical transducer is adapted for direct mechanical coupling to the middle ear in an implanted state.

4. System as claimed in claim 1, wherein the output-side electromechanical transducer is adapted for a contactless, air gap-coupling to the middle ear in an implanted state.

5. System as claimed in claim 1, wherein the electromechanical transducer has a transmission range from about 100 Hz to about 10 kHz.

6. System as claimed in claim 1, wherein the electromechanical transducer is tuned to have a first mechanical resonant frequency at an upper end of a desired transmission frequency range.

7. System as claimed in claim 1, wherein the desired transmission frequency range to which the electromechanical transducer is tuned is from about 8 kHz to about 10 kHz.

8. System as claimed in claim 1, wherein the electromechanical transducer is hermetically sealed.

9. System as claimed in claim 8, wherein said at least one sensor comprises a plurality of the acoustic sensors with an analog-digital converter connected to the output thereof.

10. System as claimed in claim 1, wherein the signal processing unit has a preprocessing arrangement for providing at least one function selected from the group consisting of pre-amplification, pre-amplification and filtering, filtering or analog-digital (A/D) conversion of the acoustic sensor signals.

11. System as claimed in claim 1, wherein the signal processing unit contains software modules which enable tinnitus masking parallel to hearing aid operation.

12. System as claimed in claim 11, wherein the digital signal processor contains software modules for controlling the electromechanical transducer and the stimulation electrode array in a manner configuring spectral, time, amplitude-referenced and phase-referenced transducer and stimulation electrode signal properties for achieving optimum hearing success in a patient-specific manner.

13. System as claimed in claim 12, wherein the software modules are static containing results of scientific findings that are stored in a program storage of the digital signal processor and remain unchanged.

14. System as claimed in claim 12, wherein the software modules are adaptively dynamic.

15. System as claimed in claim 14, wherein the software modules are adaptive for parameter matching by implant wearer training.

16. System as claimed in claim 12, wherein the digital signal processor contains a software module for optimized approximation of stimulation via an adaptive neural network.

17. System as claimed in claim 16, wherein the neural network is adaptable to training by the implant wearer.

18. System as claimed in claim 11, wherein a rewritable implantable storage arrangement for storage and retrieval of an operating program is assigned to the signal processor, and wherein at least parts of the operating program are replacable by data transmitted from an external unit via telemetry means.

19. System as claimed in claim 18, further comprising a buffer storage arrangement for buffering data transmitted from the external unit via the telemetry means before said data are relayed to the signal processor.

20. System as claimed in claim 19, further comprising checking logic for checking data stored in the buffer storage arrangement before relaying said data to the signal processor.

21. System as claimed in claim 20, wherein the checking logic and the buffer storage arrangement are implemented in a microprocessor module.

22. System as claimed in claim 19, wherein the buffer storage arrangement comprises at least two storage areas for storage and retrieval of data transferred from an external unit via telemetry means.

23. System as claimed in claim 18, further comprising at least two storage areas for storage and retrieval of at least the operating program of the signal processor.

24. System as claimed in claim 11, further comprising a microprocessor module for control of system components via a data bus, said components being selected from the group consisting of an A/D converter, a D/A converter and said signal processor.

25. System as claimed in claim 24, wherein either of program parts and an entire software module are transferrable between an external unit, the microprocessor module and the signal processor via the data bus and telemetry means.

26. System as claimed in claim 24, wherein an implantable storage arrangement for storing a working program for the microprocessor module is assigned to the microprocessor module, and at least parts of the working program for the microprocessor module are replacable by data transferred from an external unit via telemetry means.

27. System as claimed in claim 1, wherein the signal processing unit comprises a digital signal processor which provides at least one function selected from the group consisting of processing A/D-converted acoustic sensor signals and generation of digital signals for tinnitus masking.

28. System as claimed in claim 27, wherein the electromechanical transducer and the at least one electrode of the stimulation electrode array have a digital-analog converter connected upstream thereof.

29. System as claimed in claim 27, wherein a preprogrammed read-only memory area which cannot be overwritten is assigned to the signal processor.

30. System as claimed in claim 27, further comprising telemetry means for transmission of operating parameters between an implanted part of the system and an external unit.

31. System as claimed in claim 1, further comprising at least one digital-analog converter which is connected to an input of the output-side stimulation arrangement.

32. System as claimed in claim 1, further comprising a wireless telemetry means for transmission of data between an implanted part of the system and an external unit.

33. System as claimed in claim 1, wherein the electrical power supply unit comprises a rechargeable electrical storage element; wherein a wireless, transcutaneous charging device is provided for charging of the storage element; and wherein the system is adapted to be totally implantable except for said transcutaneous charging device.

34. System as claimed in claim 1, further comprising a wireless remote control for control of system functions by an implant wearer.

35. System as claimed in claim 1, wherein said system is only partially implantable; wherein said at least one acoustic sensor, said electronic signal processing arrangement, said power supply unit and a modulator/transmitter unit are contained in an external module which is externally wearable by an implant user; and wherein an implantable part of the system is passive in terms of energy and receives transducer control data and operating energy via the modulator/transmitter unit in the external module.

36. System as claimed in claim 1, the system is binaural for rehabilitation of a hearing disorder of both ears, having two system units, one for each of the two ears of a user.

37. System as claimed in claim 36, wherein the two system units are essentially identical to one another.

38. System as claimed in claim 36, wherein one system unit is a master unit and the other system unit is a slave unit which is controlled by the master unit.

39. System as claimed in claim 36, further comprising a wired implantable line connection via which the signal processing module of the units communicate with one another for optimizing binaural signal processing and transducer array control.

40. System as claimed in claim 36, further comprising a wireless connection via which the signal processing module of the units communicate with one another for optimizing binaural signal processing and transducer array control.

41. System as claimed in claim 36, further comprising ultrasonic couplers via which the signal processing module of the units communicate with one another via an ultrasonic path coupled by bone conduction, in an implanted state, for optimizing binaural signal processing and transducer array control.

42. System as claimed in claim 36, wherein implantable electrodes are assigned to the signal processing module of the units, said electrodes being adapted to form part of a data transmission path which leads through body tissue of an implant wearer in an implanted state for communication between the signal processing modules of the two system units.

* * * * *